(12) United States Patent
Jonsson

(10) Patent No.: US 7,073,936 B1
(45) Date of Patent: Jul. 11, 2006

(54) METHOD AND DEVICE FOR FEEDING COMPONENTS FOR BONE CEMENT INTO A MIXING VESSEL

(75) Inventor: Sören Jonsson, Linköping (SE)

(73) Assignee: Cemvac System AB, Falkenberg (SE)

( * ) Notice: Subject to any disclaimer, the term of this patent is extended or adjusted under 35 U.S.C. 154(b) by 0 days.

(21) Appl. No.: 08/968,034

(22) Filed: Nov. 12, 1997

Related U.S. Application Data

(63) Continuation of application No. 08/734,817, filed on Oct. 22, 1996, now abandoned, which is a continuation-in-part of application No. 08/545,591, filed as application No. PCT/SE94/00415 on May 6, 1994, now abandoned.

(30) Foreign Application Priority Data

May 10, 1993 (SE) ............................................. 9301599

(51) Int. Cl.
*B01F 13/06* (2006.01)
*B01F 15/02* (2006.01)

(52) U.S. Cl. .................... 366/139; 366/163.1; 366/189; 366/332; 366/256

(58) Field of Classification Search ................ 366/139, 366/163.1, 189, 194, 195, 242, 243, 255, 366/256, 332, 333, 602

See application file for complete search history.

(56) References Cited

U.S. PATENT DOCUMENTS

| | | | |
|---|---|---|---|
| 1,211,426 A | * | 1/1917 | Farrington |
| 3,036,819 A | * | 5/1962 | Peterson |
| 4,463,875 A | | 8/1984 | Tepic |
| 4,676,406 A | * | 6/1987 | Frischmann et al. ........ 366/256 |
| 4,966,601 A | | 10/1990 | Draenert |
| 5,100,241 A | | 3/1992 | Chan |
| 5,193,907 A | | 3/1993 | Faccioli et al. |
| 5,252,301 A | * | 10/1993 | Nilson et al. ............... 366/256 |

(Continued)

FOREIGN PATENT DOCUMENTS

| | | | |
|---|---|---|---|
| JP | 6-100056 | * | 4/1994 |
| SE | 510 490 | | 5/1999 |
| WO | WO 93/22041 | * | 11/1993 |
| WO | WO 94/05415 | * | 3/1994 |
| WO | WO 94/26403 | * | 11/1994 |
| WO | WO 97/18031 | * | 5/1997 |
| WO | WO 99/67015 | | 12/1999 |

*Primary Examiner*—Tony G. Soohoo
(74) *Attorney, Agent, or Firm*—Merchant & Gould P.C.

(57) ABSTRACT

A method and an arrangement for successively feeding batches into a mixing vessel under partial vacuum for the preparation of bone cement. The arrangement includes an inner container communicating with the atmosphere and with the mixing vessel, which container is so arranged as to enclose a glass ampoule containing a liquid bone cement component and, on the other hand, a device for opening the ampoule so that its contents can be sucked into the mixing vessel under partial vacuum. An outer container encloses the inner container at least partially, and is arranged to communicate with the mixing vessel. The inner container, and the outer container, define a space filled with a proportional quantity of a second bone cement component, which is in powder form. The inner container is capable of displacement relative to the outer container between a first position, in which sections of the inner container prevent communication between the mixing vessel and the atmosphere, and a second position, in which communication between both the mixing vessel and the atmosphere is open, so that the powdered bone cement component can be sucked into the mixing chamber under vacuum. The feeding sequence of the bone cement components is arbitrary. In other embodiments, the inner and outer containers are eliminated, or only the inner container is retained.

19 Claims, 18 Drawing Sheets

U.S. PATENT DOCUMENTS

| | | | |
|---|---|---|---|
| 5,328,262 A | | 7/1994 | Lidgren et al. |
| 5,549,380 A | | 8/1996 | Lidgren et al. |
| 5,779,356 A | * | 7/1998 | Chan .......................... 366/139 |
| 5,797,678 A | * | 8/1998 | Murray ....................... 366/139 |
| 5,852,241 A | | 12/1998 | Fagerdahl et al. |
| 5,934,803 A | * | 8/1999 | Hutter ........................ 366/139 |
| 6,017,349 A | * | 1/2000 | Heller et al. .................. 606/92 |
| 6,042,262 A | * | 3/2000 | Hajianpour ................. 366/139 |
| 6,120,174 A | * | 9/2000 | Hoag et al. ................. 366/139 |
| 6,176,607 B1 | * | 1/2001 | Hajianpour ................. 366/139 |
| 6,312,149 B1 | * | 11/2001 | Sjovall et al. .............. 366/139 |

\* cited by examiner

METHOD AND DEVICE FOR FEEDING COMPONENTS FOR BONE CEMENT INTO A MIXING VESSEL This application is a continuation of application Ser. No. 08/734,817, filed Oct. 22, 1996, now abandoned, which is a continuation-in-part of Ser. No. 08/545,591 filed Nov. 13, 1995, now abandoned which is based on PCT/SE94/00415 filed May 6, 1994.

BACKGROUND OF THE INVENTION

1. Field of the Invention

The present invention relates to a method for successively feeding batches of constituent components into a mixing vessel for the preparation of bone cement under vacuum. The invention also relates to an apparatus for successively feeding batches of constituent components into a mixing vessel under partial vacuum for the preparation of bone cement.

2. Description of the Prior Art

Bone cement is prepared by mixing polymethyl methacrylate in powder form with liquid monomethylmethacrylate in a mixing container. Both the liquid component and the combined mixture give off substances in gaseous form which are environmentally harmful and injurious to human health. For this reason, it is important for the introduction of the bone cement components into the mixing container and the mixing process itself, to take place in such a way that the smallest possible quantity of the harmful gases escape into the surrounding environment. Mixing vessels have been developed where the introduced components were successfully prepared into bone cement without a substantial release of the aforementioned gases. However, in order for the bone cement to develop its optimal strength during use, it is also important for the components comprising the cement to have well-mixed, predetermined proportions.

SUMMARY OF THE INVENTION

The object of the present invention is to make available a method and device of the kind described above, which avoids the risk of gas release when feeding the bone cement components into the mixing vessel. This is achieved in accordance with the invention in a number of ways. According to one method, a glass ampoule containing a liquid component of a bone cement is surrounded by a container which is in reclosable communication with the atmosphere. A second container surrounds the first container so that when the mixing vessel is opened, the contents of the ampoule, under the effect of a partial vacuum inside the mixing vessel, can be sucked down into it, in that a space between the aforementioned inner container and outer container is filled with a second bone cement component in powder form which is caused by displacement of the inner container relative to the outer container, to move from a first position in which the space does not communicate with the atmosphere or the mixing vessel, then to a second position in which the space communicates with the atmosphere and the mixing vessel, so that the powdered bone cement component is sucked down into the mixing vessel under the effect of the partial vacuum inside it.

A device for carrying out the above method in accordance with the invention is characterized in that it comprises an inner container communicating with the atmosphere, and is so arranged as to enclose the glass ampoule containing the liquid bone cement component, and to communicate with the aforementioned mixing vessel, and which includes means for opening the ampoule so that its contents, under the effect of the partial vacuum inside the mixing vessel, can be sucked into it. The outer container at least partially encloses the inner container and is also arranged so as to communicate with the mixing vessel and together with the inner container, defines a space therebetween which is filled with a certain quantity of the powdered component of the bone cement. The inner container is capable of displacement from a first position to a second position, the first position characterized by the inner container preventing communication between both the mixing vessel and the atmosphere, and the second position characterized, in which communication between the mixing vessel on the one hand the the atmosphere on the other hand is open, so that the bone cement component in powder form, under the effect of the partial vacuum inside the mixing vessel, can be sucked into it without escape of gases.

According to another method, which has a couple of variants, the outer or second container is eliminated and the mixing vessel is prefilled with the powder bone cement component. The first container holding the ampoule of the liquid bone cement component connects to the mixing vessel in a manner where displacement of a container cap causes the liquid component to be sucked into the mixing vessel under vacuum.

According to yet another method, the first and second containers are eliminated and the liquid bone cement component is supplied through a collapsible plastic bag and tubing arrangement attached thereto. The tubing can be connected to the mixing vessel in at least two convenient locations, where a tubing clamp is released to allow the liquid component to flow into the mixing vessel under pressure.

Along the same lines of eliminating the first and second containers, another method of the present invention simply involves a providing a glass ampoule with the liquid component therein, breaking the ampoule, and then supplying the contents into the mixing vessel through a funnel attached thereto. Again the liquid component is sucked under vacuum into the mixing vessel.

A final method of the present invention again involves use of a first container for holding an ampoule, but now the container is melded to the mixing tube for directly draining into the bottom of the mixing vessel.

The devices for carrying out all methods in accordance with this invention are more fully detailed in the following sections.

BRIEF DESCRIPTION OF THE DRAWINGS

The invention is described below in greater detail with reference to the accompanying drawings, in which.

DETAILED DESCRIPTION OF THE INVENTION

Figure 1:
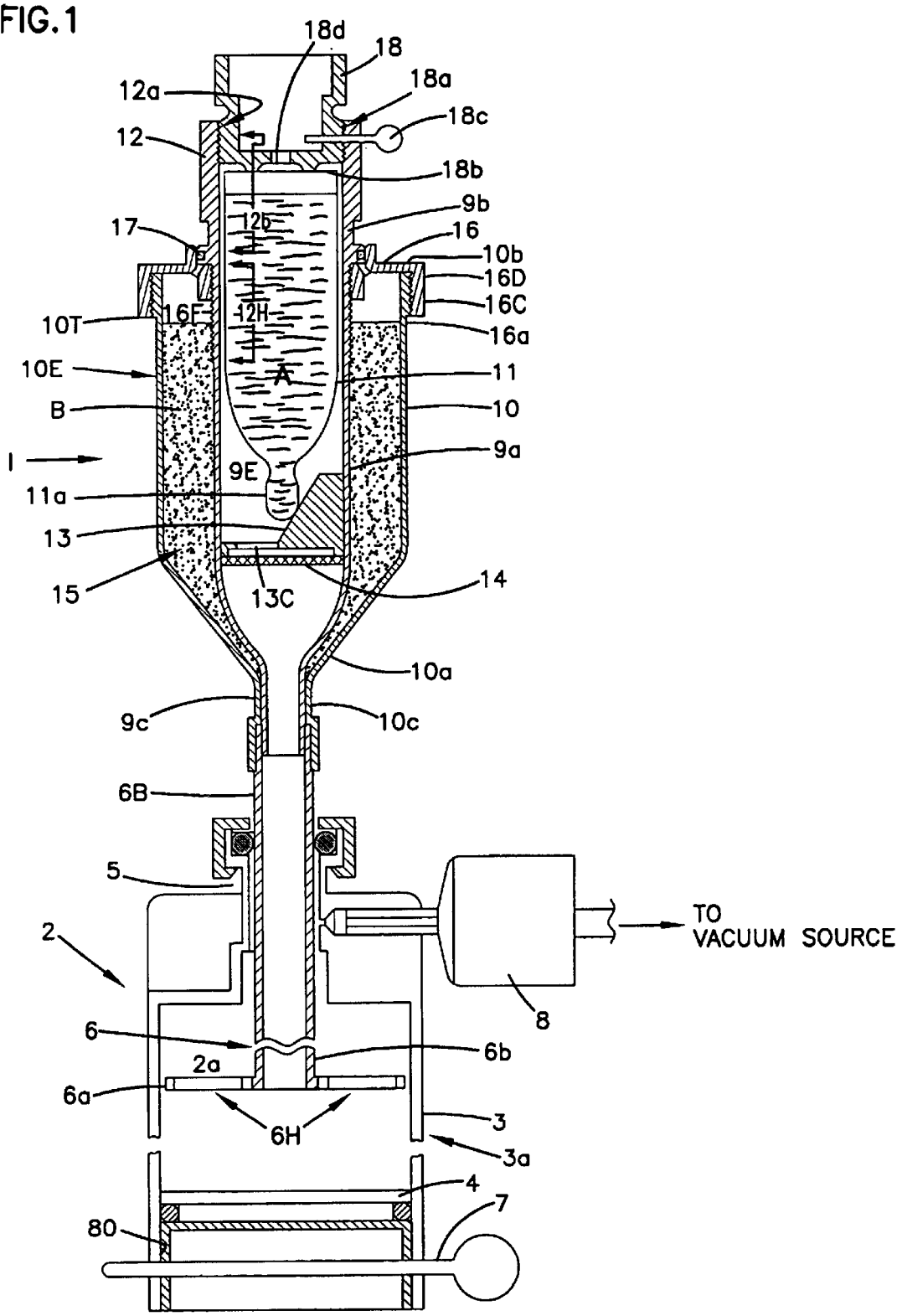
FIG. 1 is a cross-sectional view in longitudinal section of an embodiment of a feeding/mixing device of the present invention with the mixing vessel filled with bone cement components in liquid and powder form, prior to mixing.

The designations 1 and 2 are used generally in the drawings in respect of a feed arrangement and a mixing vessel. The latter comprises an interior 2a, a cylindrical container 3 comprised of an outer cylinder wall 3a, a bottom 4 at one end of the container and a spout 5 with a sealed opening at the other end, together with an agitator 6, received within said spout and mixing vessel and capable of axial, vertical movement inside the container 3. The agitator 6 consists of an agitator disc 6a attached to a tubular agitator rod 6b. The agitator 6 is mounted so that it is free to vertically slide up and down while maintaining a seal in the spout 5, in such a way that the plurality of holes 6h in agitator disk 6a can be used to bring about through mixing of the bone cement components within mixing vessel 2 has been removed, the bottom 4 can be axially displaced inside the cylinder by upward movement of piston head 80, moving towards the spout 5. The piston-like function of bottom 4, upwardly pushes and then discharges the mixed bone cement via the hollow agitator rod 6b, which now serves as a discharge nozzle. The interior of the container 2 communicates via a filter 8 with a vacuum source (not shown) during feeding and mixing of the bone cement components. Rapid and effective feeding of the bone cement components into the mixing vessel, and safe handling of the gases that are environmentally harmful and injurious to human health, are achieved in this way.

The feeding of the bone cement components from the feed arrangement 1 into the mixing vessel 2 takes place via the agitator rod 6b, and the details concerning the component mixing within vessel 2 will be described later.

Figure 2:
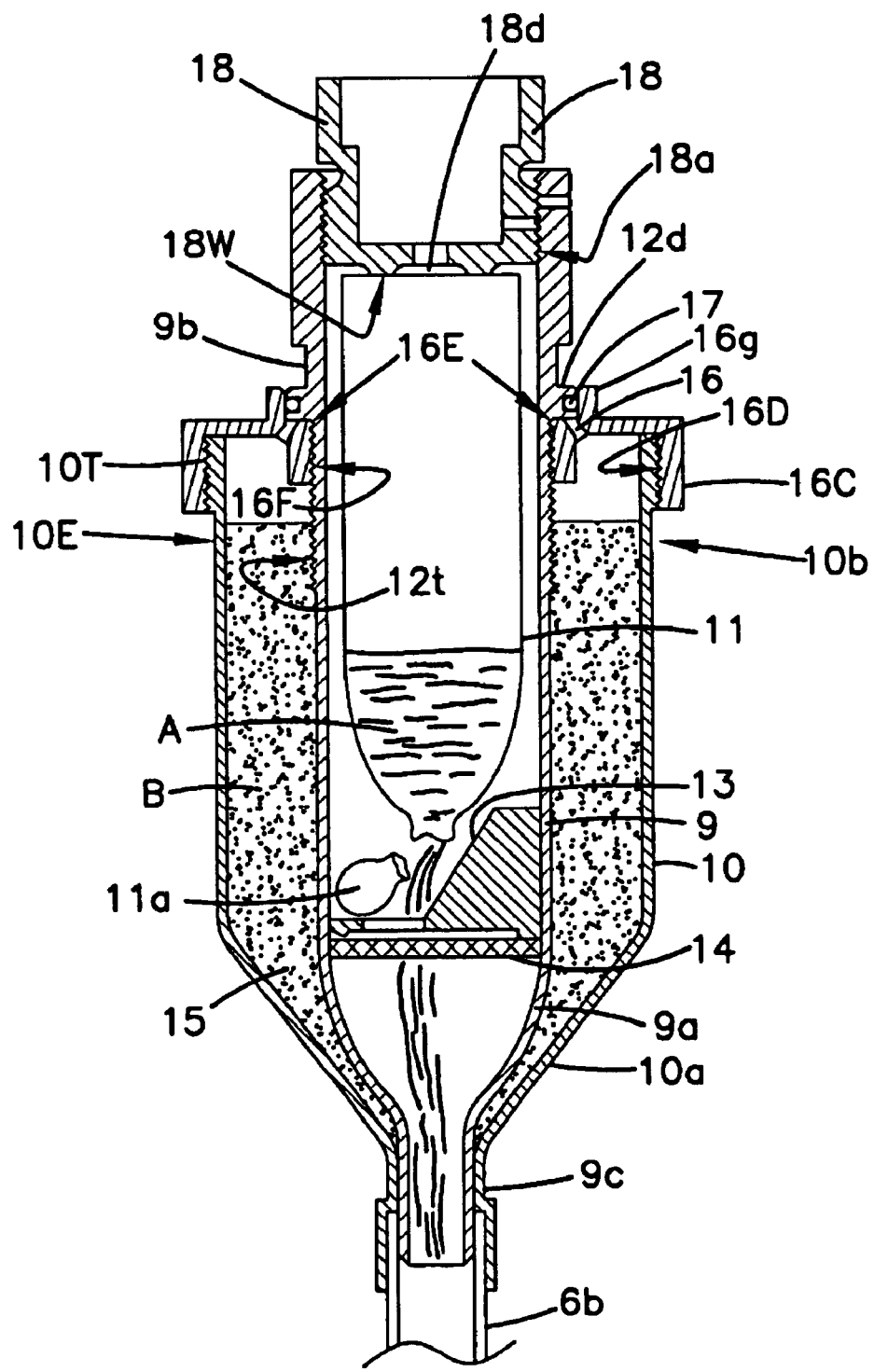
FIG. 2 illustrates the feeding of the liquid bone cement component into the mixing vessel.
Figure 3:
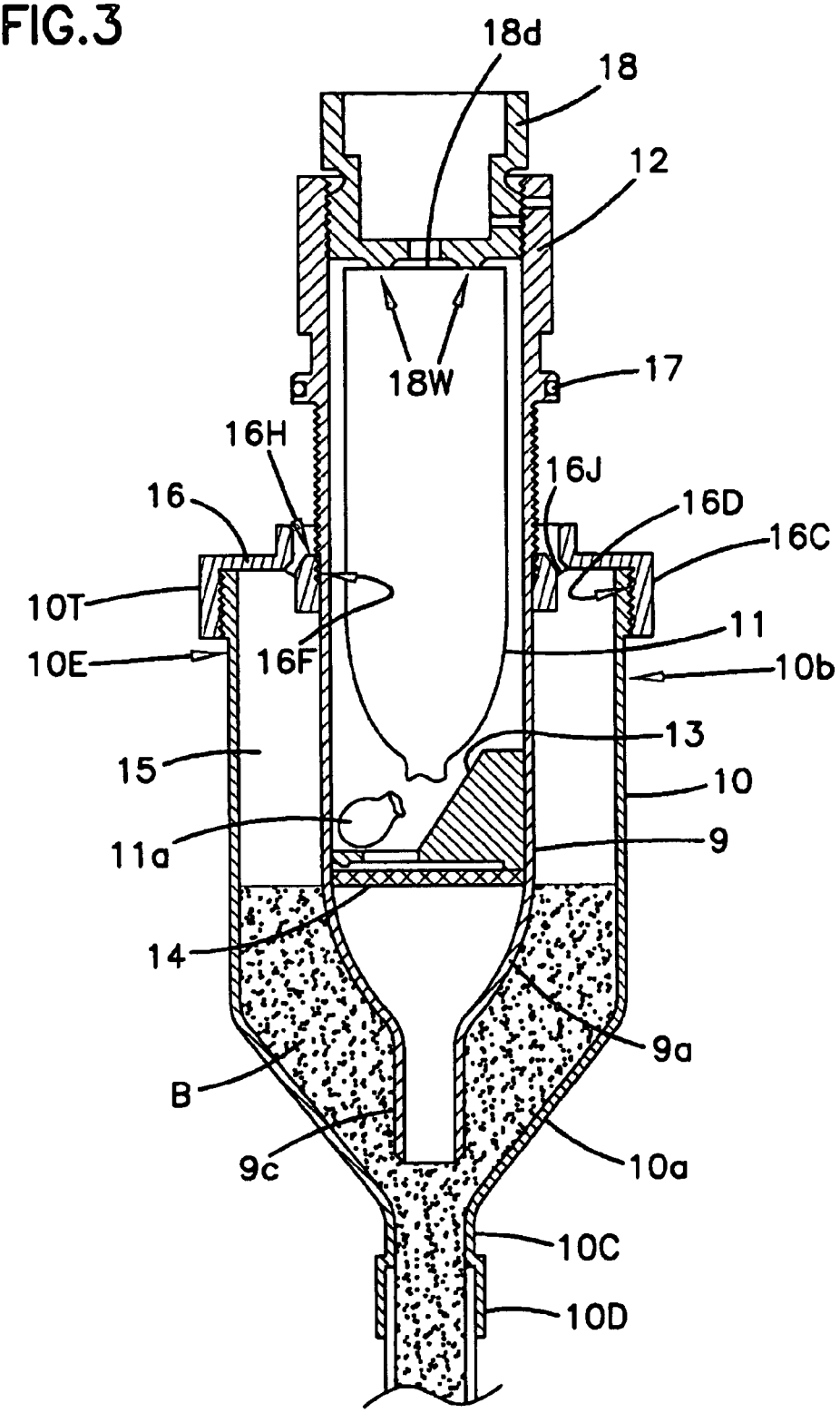
FIG. 3 illustrates the feeding of the powder bone cement component into the mixing vessel.

The feed arrangement 1 of the first embodiment, shown in FIGS. 1–3, comprises an inner, essentially cylindrical container 9 communicating with the atmosphere and an outer, similar cylindrical container 10 which at least partially encloses the inner container. The container interior 9e is so arranged so as to enclose a glass ampoule 11 containing the liquid bone cement component A, and to communicate with the mixing vessel 2, via its agitator rod 6b, as already mentioned. The container 9 is integrally formed having a cylindrical collar 12 about its bottom end 9b with a threadable cap 18 capable of axial displacement relative to it. Removal of cap 18 allows insertion of ampoule 11 within interior 9e.

In the embodiment illustrated in FIG. 1, the facility for displacement to take place between the cylindrical collar 12 and the cap 18 is achieved by means of the internal collar threads 12a engaging the external cap threads 18a. The cap 18 has an opening 18d communicating between the interior 9e of the container 9 and the atmosphere, and the container 9 has a funnel-shaped top end 9a, with the narrow neck portion 9c having an outside diameter which frictionally inserts within, and discharges into the open agitator rod 6b. In the first embodiment in accordance with FIGS. 1–3, a tip 11a of the glass ampoule 11 points downwards, and there is present inside the interior 9e of container 9, a glass ampoule breaking means 13 in the form of an oblique plane 13a. Tip 11a of the glass ampoule 11, which has a fractural impression therein, rests against means 13. The bottom 18b of the cap has an annular raised wall 18w, which contacts ampoule 11, thereby clamping it between means 13 and cap 18. When cap 18 is screwed axially downwards, the tip 11a is eventually broken off against the oblique plane 13a, and the contents of the ampoule are sucked downwardly through opening 13c of means 13, into the mixing vessel 2 by the partial vacuum existing inside of it, as illustrated in FIG. 2. A filter 14 is provided for the purpose of preventing glass splinters from the glass ampoule 11 accompanying the contents into the mixing vessel 2. In the second and third embodiment in accordance with FIGS. 4–6, the tip 11a of the glass ampoule points upwards, and the inner container 9 has a glass breaking means 13 in the form of an upward-facing and pointed cone 13b, against which the bottom 11b of the glass ampoule rests. The bottom 18b of the cap 18 is formed with vertically taller walls 18w, such that they contact ampoule 11, thereby clamping it in place. When cap 18 is screwed downwards, the bottom 11b of the glass ampoule 11 is penetrated by the cone 13b and, as previously described for the first embodiment, the contents of the glass ampoule are sucked downwardly through openings 13c, then into the mixing vessel 2. A filter 14 can also be provided. As the liquid bone cement component of the glass ampoule 11 flows down into the mixing vessel 2, air is sucked in via the opening 18d thereby sealing and preventing the gases from the liquid bone cement component from escaping into the atmosphere.

The outer container 10 is generally similar in shape to the inner container 9, with container 9 being concentrically arranged within at least a part of container 10. Outer container 10 also has a top end formed as a funnel-shaped part 10a, with a reduced neck member 10c that has an inside diameter slightly larger than the outside diameter neck 9c of inner container 9 so that neck 9c is also frictionally contacting neck member 10c. The neck 10c has a flared end 10d which inserts over the open end of agitator rod 6b. A space 15 exists between containers 9 and 10, and the powder component B of the bone cement is to be received therebetween prior to mixing. The bottom 10b of container 10 10 has an outer surface 10e that is formed with threads 10t. Threads 10t are in threaded engagement with the internal threads 16d on downwardly depending edge 16c of interlocking cap 16, thereby closing the top of container 10. The central throughbore 16e includes threads 16f for threadingly receiving inner container bottom collar 12. In this way, when inner container 9 is threaded downwardly by engaging threads 12t against throughbore threads 16f, grooved annular flange 12d is seated against annular seat 16h. At the same time, O-ring 17 creates a seal against the annular upstanding lip 16g. When in this first position, the outer container is sealed at its bottom end from the atmosphere. When inner container 9 is axially displaced within the interlocking cover 16, in an opposite direction, this seal is broken. Comparing FIGS. 2 and 3, it is seen that the inner container is now upwardly displaced in the axial direction wherein, the funnel-shaped tops 9a and 10a disengage each other and the containers no longer form a closure of the space 15 at the necks 9c and 10c. The inner container is raised until the threads 12t are run-out, so that container 9 now allows the space 15 to communicate with the inside 2a of the mixing vessel. In the latter position, channels 16j are now opened in communication with the atmosphere, facilitating the introduction of the powder component of the bone cement out of space 15 and into vessel 2, through the partial vacuum inside the mixing vessel. Air allowed into container 10 prevents the aforementioned gases from finding their way into the atmosphere.

Figure 4:
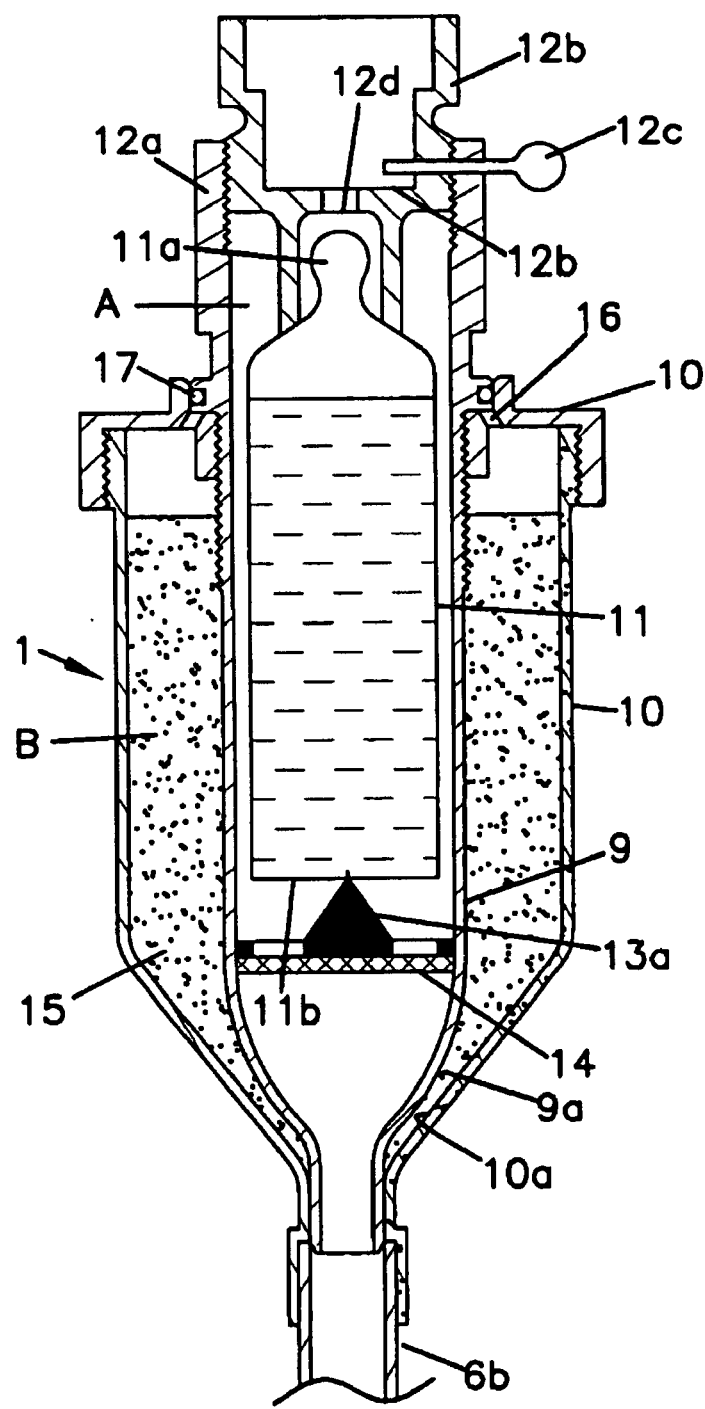
FIG. 4 illustrates a second embodiment of the invention in longitudinal cross-section.
Figure 5:
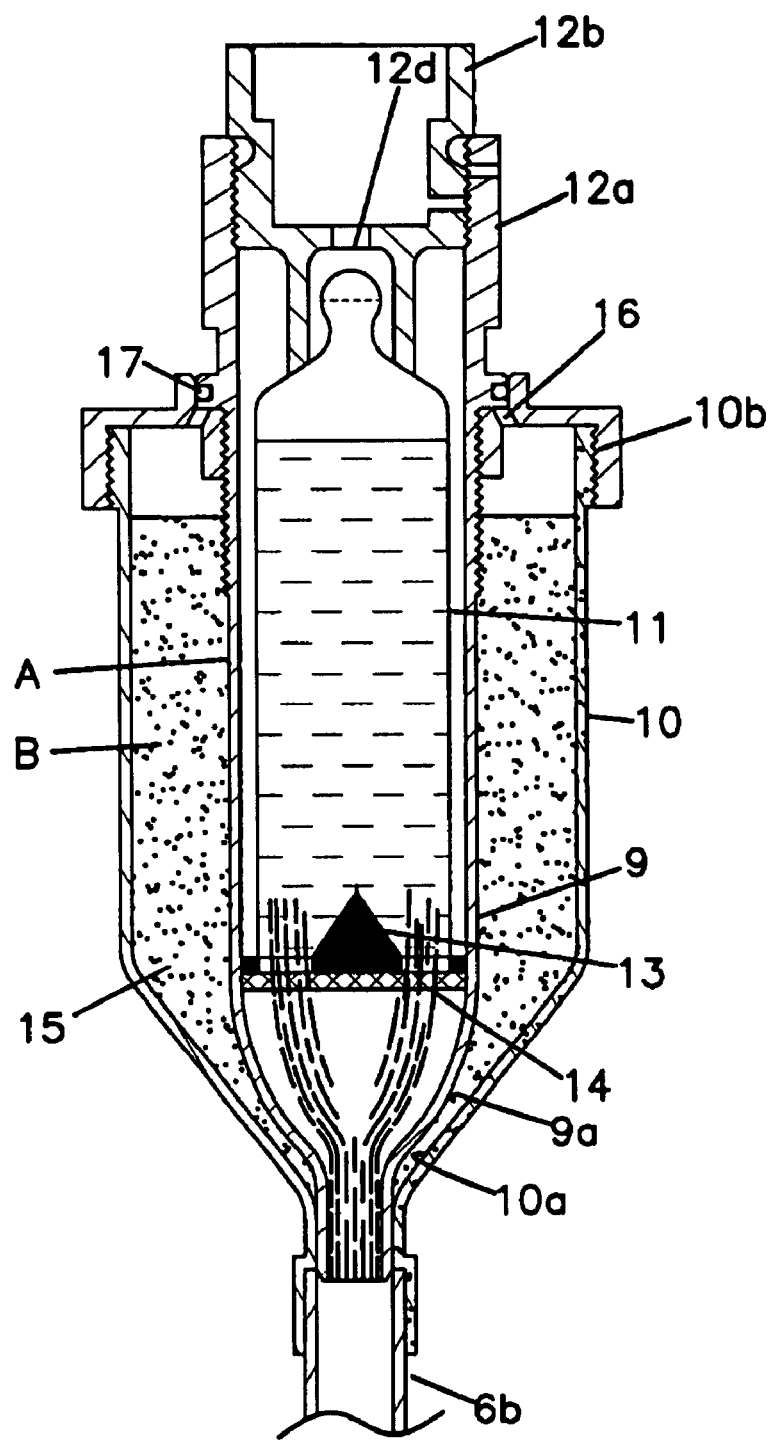
FIG. 5 illustrates feeding the liquid bone cement component into the mixing vessel of FIG. 4.
Figure 6:
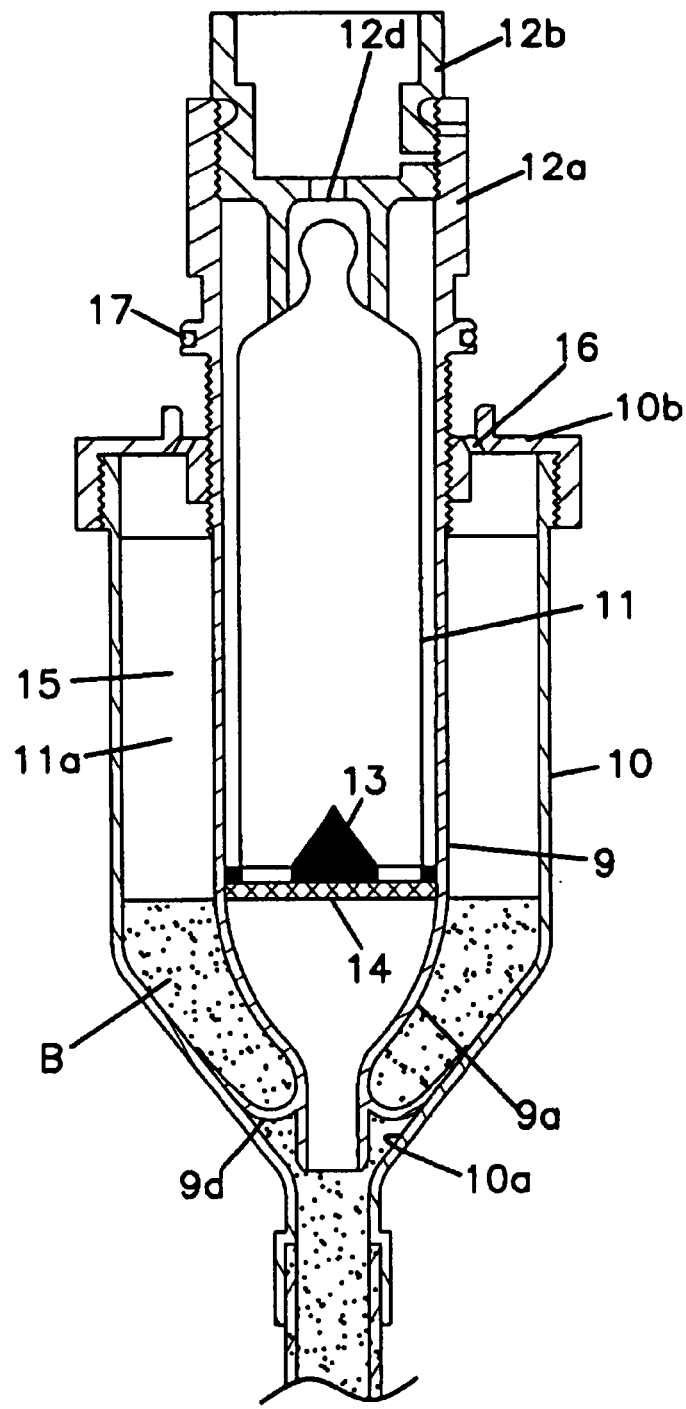
FIG. 6 illustrates a third embodiment of the present invention where feeding the powder component into the mixing vessel differs slightly from that of FIG. 4.
Figure 7:
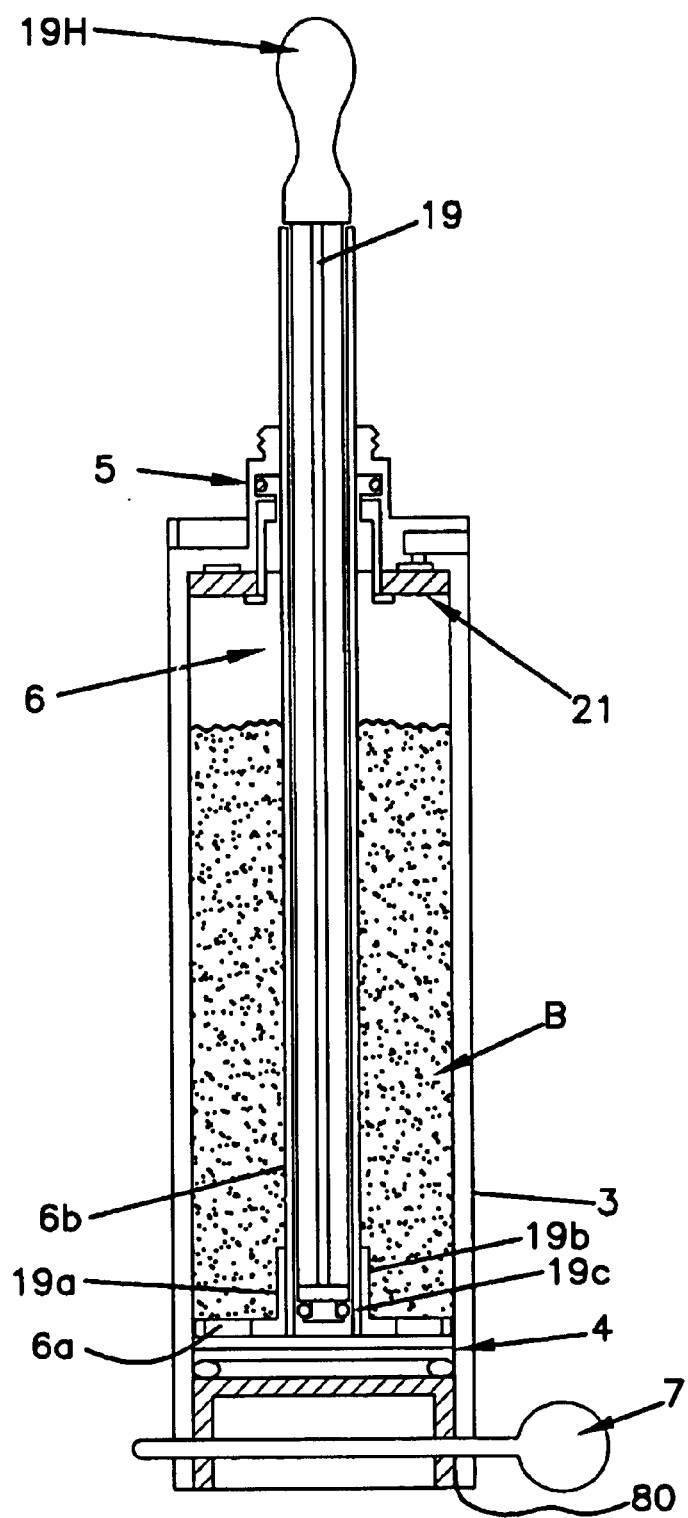
FIG. 7 illustrates the mixing vessel of a fourth embodiment of the present invention in which the powder form of the bone cement pre-exists within the mixing vessel.

The third embodiment in accordance with FIG. 6, shows that the only difference between this embodiment and the embodiments of FIGS. 4 and 5, is found in the brush-shaped devices 9d which are arranged as to make contact with the surface of the funnel-shaped part 10a in the first position of container 9. The bone cement component B is released from the aforementioned surface by relative rotation between the outer and inner containers such that trushes 10d, under weight of the powder, collapse and allow powder to fall into tube 6b.

A feed procedure of the above-described embodiments will now be summarized below with reference to FIGS. 1–6 of the drawings. It should be understood that with these embodiments, the feed arrangement is supplied ready for use, meaning it is filled with the bone cement components in the correct proportions.

As FIG. 1 illustrates, in order to permit feeding of the bone cement components into the mixing vessel 2 from the feed arrangement 1 in accordance with the invention, the mixing vessel 2 is required to be connected to an active vacuum source. The pin 18c is first removed, and the displaceable cap 18 is screwed downwards, wherein the glass ampoule 11 is also caused to move downwards. Screwing continues until the tip 11a of the glass ampoule 11 is broken off against the breaking means plane 13a (See FIG. 2), or until the bottom 11b of the glass ampoule is penetrated by the tip of the cone 13b (See FIG. 5). The liquid bone cement component now flows down into the mixing chamber 2 under the effect of the partial vacuum existing inside of it. Once the glass ampoule 11 is totally empty, the cylindrical collar 12 is rotated from the first and sealed position so that the inner container 9 is axially displaced upwards to the second position shown in FIG. 3, in which the space 15, which was previously closed at its top and sealed from the atmosphere at its bottom, is now opened at the bottom, via the channels 16j, and at the neck 9c, 10c. The powder component B of the bone cement is now allowed to drop downwardly into mixing chamber 2. Once the space 15 has been completely emptied, the entire feed arrangement 1 is removed, and the inner tubular part 6b of the agitator rod 6 is sealed with a sealing rod 19 (shown in FIG. 12) which seals the bottom second end 6e. The mixing procedure can now start.

The feed arrangement of the embodiments just described can be modified in many ways within the scope of the invention. This is true, for example, of the facility for axial displacement between the inner container 9 and its cap 18, and between the inner container 9 and the outer container 10, which facility for axial displacement can be achieved other than by threaded engagement. Also, means other than the oblique plane 13a or the pointed cone 13b can be considered for the purpose of breaking open the ampoule 11. Furthermore, the emptying sequence can also occur in the reverse order to that described above, i.e. first the powdered component of the bone cement can be dropped, and then the liquid bone cement component.

Turning attention now to FIGS. 7–12, a fourth and a fifth embodiment of the present invention will now be described. These two embodiments differ from the previously described ones from the perspective that the powdered component of bone cement pre-exists within the mixing vessel 2 prior to any mixing procedures, and that the container 9 contains only the liquid component. It will become clearer after reading the following description that the main characteristic of the fourth embodiment is that only the liquid component will be drawn into the mixing vessel under vacuum like the previous embodiments, and that a slightly different ampoule arrangement is provided wherein the contents feed downward through the tubular agitator rod 6b, and enter vessel 2 in the vicinity of the vessel bottom 4. The fifth embodiment uses a similar ampoule arrangement. However, the ampoule does not rest on the mixing vessel and the contents enter through the outer cylindrical wall 3a, also near the mixing chamber bottom 4. The fourth and fifth embodiments, as well as the sixth one described later, are also provided with a second filter 21, located at the top of mixing vessel 2.

Figure 8:
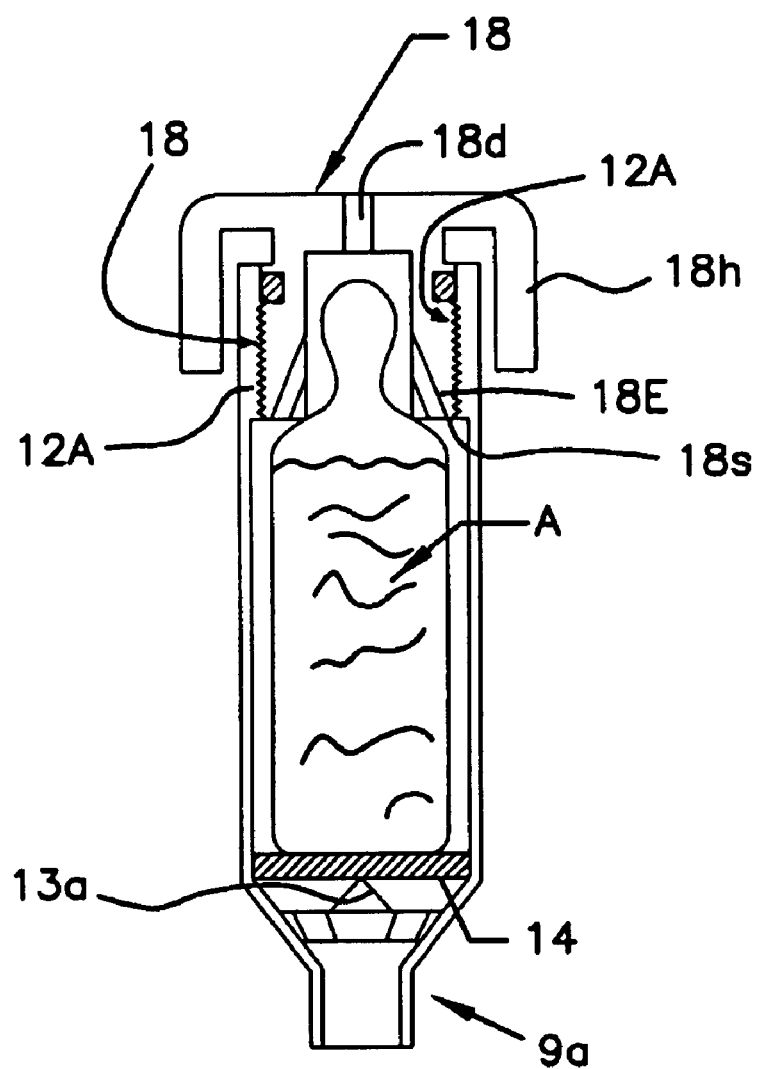
FIG. 8 illustrates a container and a cassette that houses a glass ampoule which contains the liquid form of the bone cement.
Figure 9:
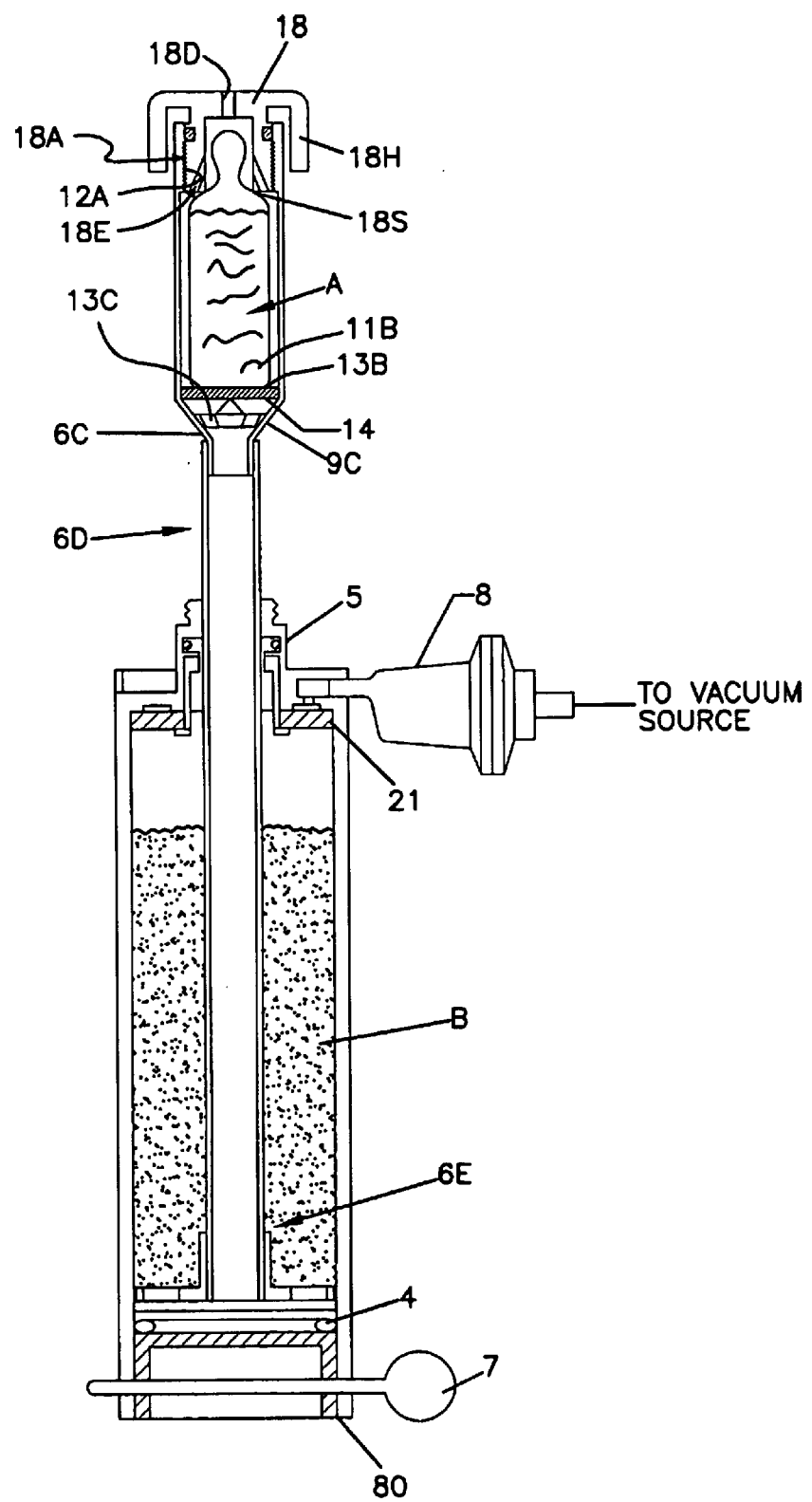
FIG. 9 illustrates a cross-sectional view of the mixing vessel of FIG. 7 prior to mixing the cement components.
Figure 10:
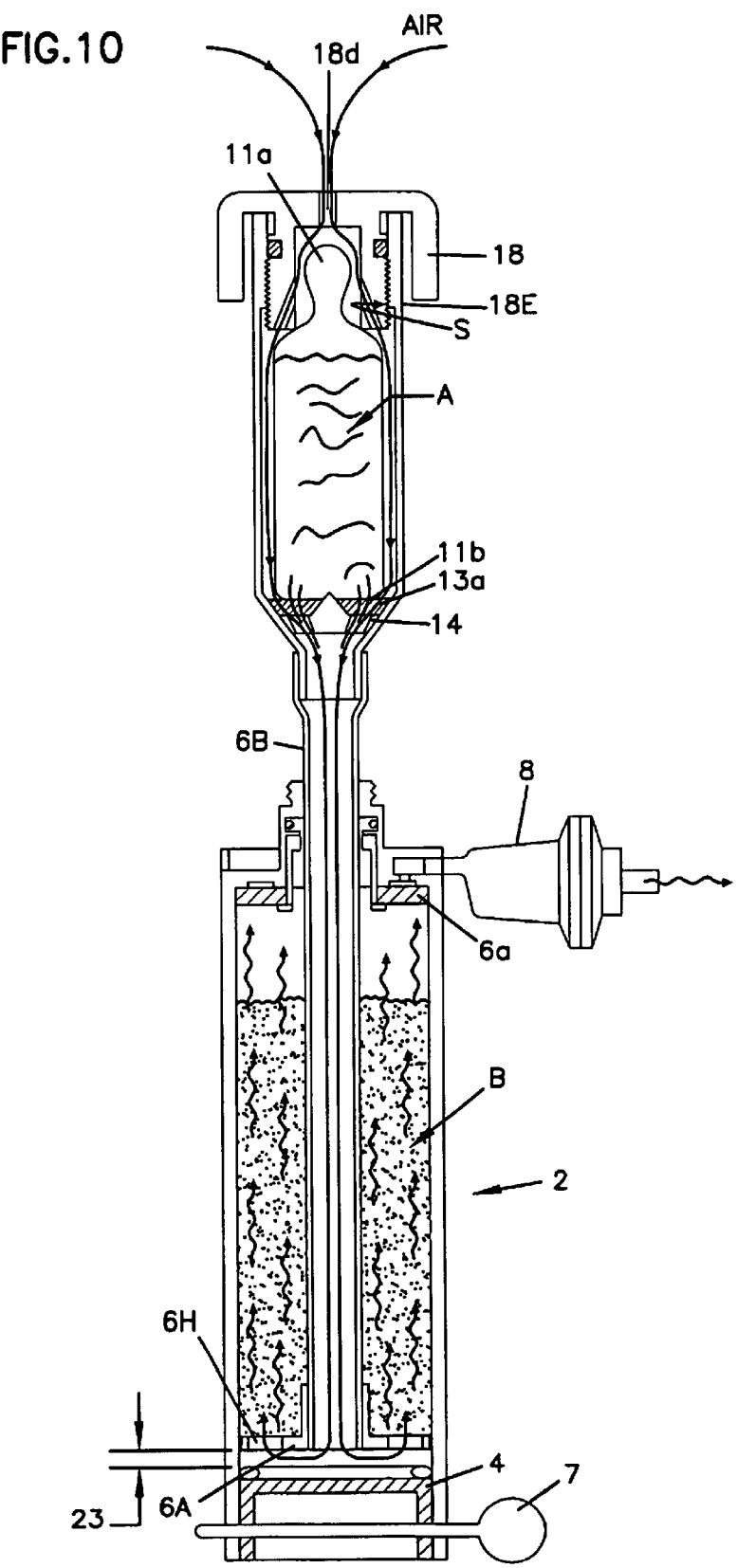
FIG. 10 illustrates the mixing vessel of FIG. 9, feeding the liquid into the vessel.
Figure 11:
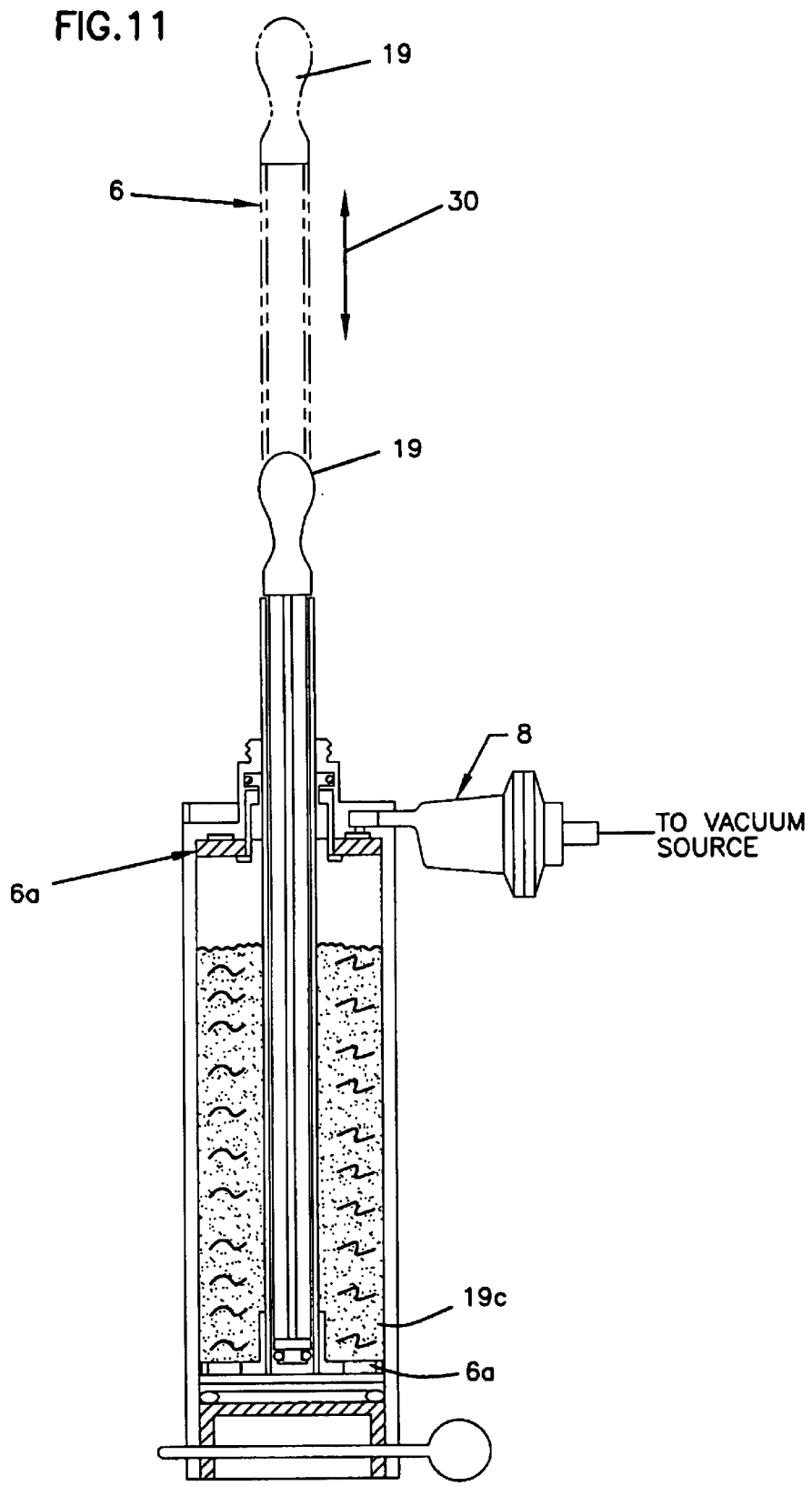
FIG. 11 illustrates the mixing vessel of FIG. 7 with the bone cement components thoroughly mixed.

In accordance with the fourth embodiment, FIGS. 7–11 show mixing vessel 2 as being pre-filled with the powder component of the bone cement. A tightening rod 19 is received within tubular agitator rod 6b of agitator 6 and has plug 19a and O-ring 19c inserted within a groove 19b thereof, to form an air-tight seal so that powdered contents B are not contacted by and affected by atmospheric air which is capable of downwardly travelling along tubular rod 6b to vessel bottom 4. Just prior to introducing glass ampoule 11 on top of mixing vessel 2, tightening rod 19 is completely removed from tube 6b, wherein the cylindrical container 9 is placed on top of vessel 2 by inserting funnel-shaped neck 9c into mouth 6c at the first end 6d of tubular rod 6b. Although FIGS. 1–6 show funnel-shaped top end 9a as having a slightly different contour from that of the same section shown in FIGS. 7–12, it should be understood that either contour can be used interchangeably in these embodiments. FIG. 8 shows in greater detail that glass ampoule tip 11a is pointing upwards when inserted within container 9, and that the ampoule is resting upon the upward cone 13b of breaking means 13, said means having internal passages 13c for allowing liquid therethrough once it passes filter 14. FIG. 8 also illustrates that cap 18 is constructed slightly modified in that cap 18 has gripping means 18h for facilitating the operative threading movement of cap 18 along container threads 12a. FIG. 9 shows the ampoule 11 just prior to being broken. FIG. 10 shows that when handle 18h of the cap is turned so as to downwardly displace the cap 18 through action of the interacting threads 12a and 18a, shoulder 18s pushes downwardly against ampoule 11, causing upward-facing, pointed cone 13b to break bottom 11b of the ampoule, thereby allowing liquid contents A to flow through filter 14 under suction downwardly into hollow tube 6b as previously described. As FIG. 10 shows, openings 18d and 18e in cap 18, allow atmospheric air to be communicated into the interior of container 9 under suction, also as previously described, thereby preventing noxious fumes escaping to atmosphere. A small gap 23 exists between vessel bottom 4 and agitator disk 6a so that as liquid A descends tubular rod 6b, exists open end 6e, then it enters gap 23, which behaves as a passage for percolating an air/liquid mixture upwardly through holes 61h in the agitator disk 6a, so that air bubbles cause liquid A to thoroughly mix with the powder component B, while under the continuing action of the vacuum source. FIG. 11 illustrates that once ampoule 11 is empty, container 9 is removed and replaced with tightening rod 19. While still under vacuum, tubular rod 6b is grasped and then successively moved up and down in the direction of arrow 30 and down with rod 19 still inserted therein, as the outlined representation in FIG. 11, so that agitator disk 6a ensures thorough mixing of the liquid and powder components, while rod 19 prevents gaseous escape from tubular rod 6b due to O-ring seal 19c. The filter 21 is provided to remove heavy particulate before it can be drawn into the vacuum source 8. Once admixed, first lock 7, and then rod 19 are removed and then bottom 4 is axially displaced within cylinder 3 in a fashion similar to a piston, as previously described, so that the mixed bone cement can be pushed out of vessel 2. In this way, agitator rod 6 is pulled completely up so that agitator disk 6a contacts the top end 3b of cylinder 3, with tubular rod 6b acting as a discharge nozzle for the now-ready cement.

Figure 12:
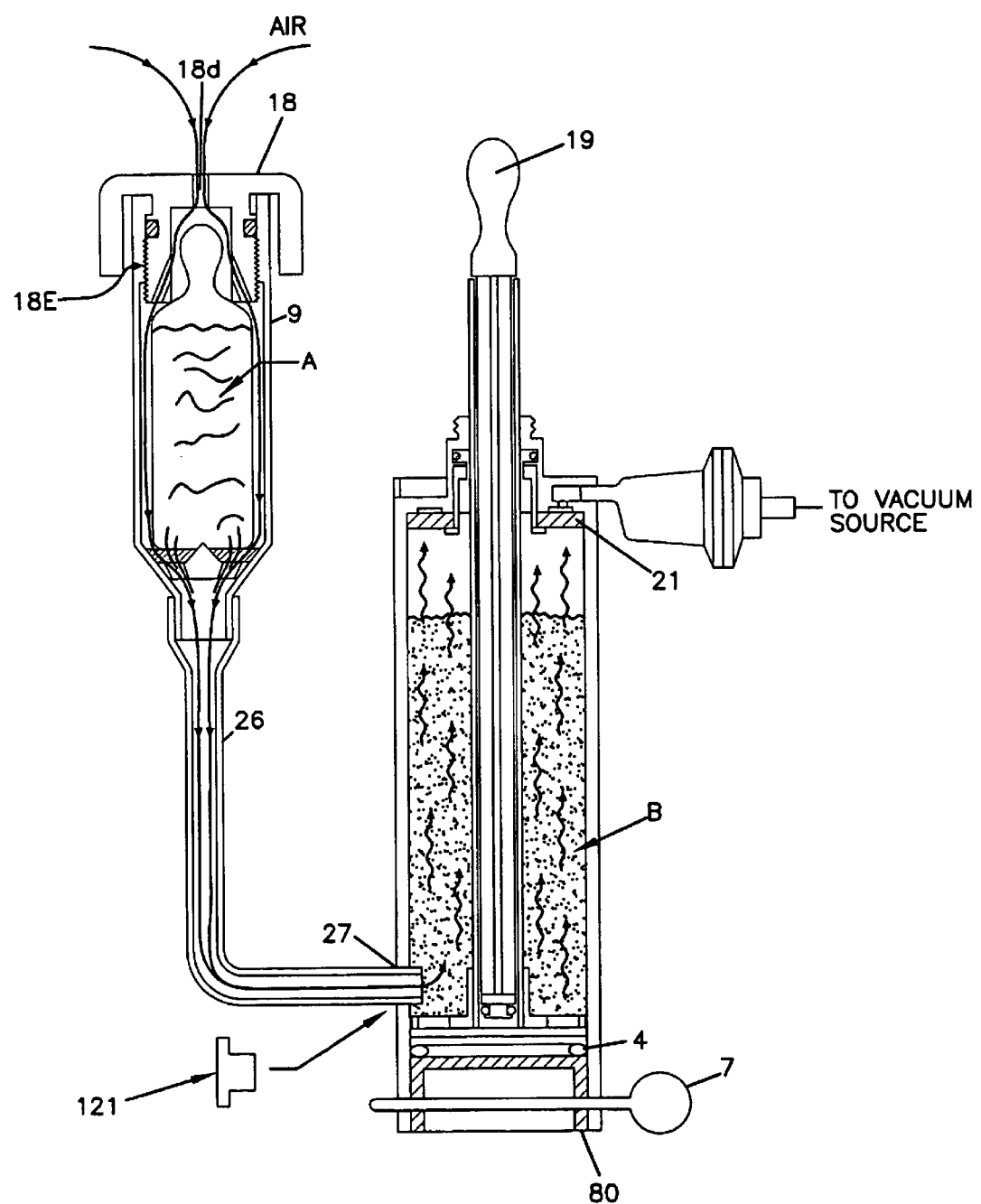
FIG. 12 illustrates the mixing vessel of a fifth embodiment of the present invention in which the liquid form of the bone cement is fed into the mixing vessel through the side wall.

FIG. 12 shows a fifth embodiment of the present invention wherein the mixing vessel is again pre-filled with powder component B and where container 9 has top end 9a connected to a tube 26, shown as being inserted into hole 27 which penetrates cylinder wall 3a. It is to be understood that prior to insertion of tube 26, plug 121 is inserted within hole 27, thereby maintaining a seal from the atmosphere. When introduction of liquid A is to take place, plug 121 is removed and then the tube is inserted into hole 27. The glass ampoule containing liquid A is broken and then by perculation of air and liquid A through powder component B in mixing vessel 2, a pre-mixing is obtained. When the ampoule is emptied, tube 26 is removed from hole 27, and plug 121 is reinserted and final mixing, by means of the agitator, is performed as previously described in connection with FIG. 4. After thorough mixing, lock 7 is removed, and the contents pushed upwards with piston head 80 for eventual discharge out tube 6b.

Figure 13:
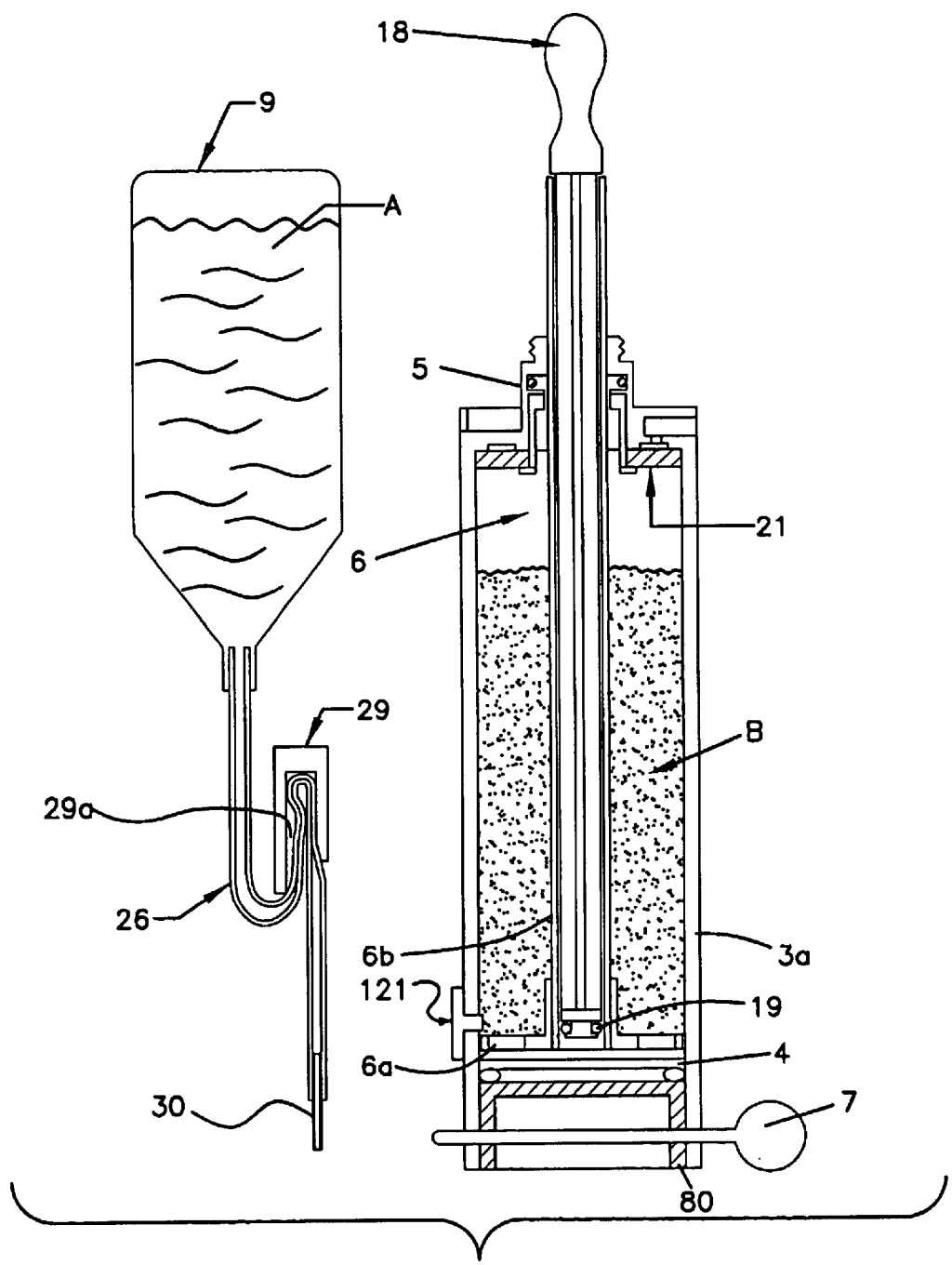
FIG. 13 illustrates the mixing vessel of a sixth embodiment of the present invention where the liquid bore cement component is contained in a collapsible plastic bag.

FIG. 13 shows a sixth embodiment, where container 9 is now comprised of a collapsible plastic bag. This substitution advantageously reduces the cost to manufacture, and is less bothersome than breaking and discarding the glass ampoule bottles. Again, this arrangement functionally mixes the elements together as previously explained. However, as seen in FIG. 13, a U-shaped sleeve member 29 is used as a valve, where tube 26 is folded and frictionally inserted within sleeve interior 29a, thereby blocking any flow of material A. Then, plug 121 is removed from cylinder wall 3a, and is inserted into hole 27. FIG. 13 shows a coupling 30 being inserted into tube 26 to facilitate the connection into the cylinder wall and to allow discharge of fluid A more centrally within mixing vessel 2 once inserted through hole 27. It should be realized that the embodiments of FIGS. 6–12 could also be provided with coupling 30 if desired. Mixing is completed by upwardly and downwardly moving agitator disk 6a as previously described, using mouth 6c of rod 6b as a discharge nozzle once desk 6a is contacted against top end 3a of cylinder 3, and tightening rod 19 is removed so that the mixed contents can be pushed upwards by bottom 4.

Figure 14:
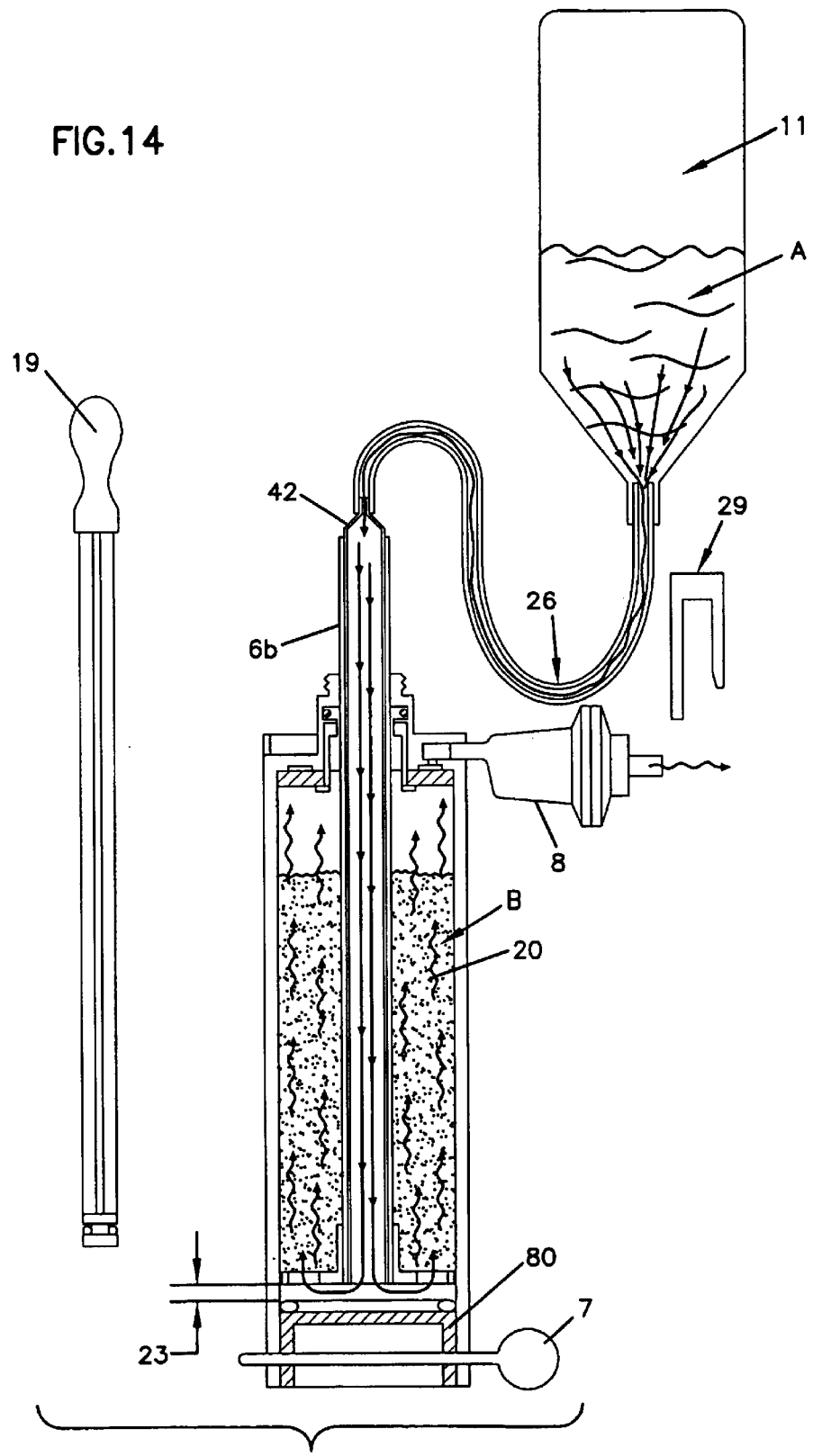
FIG. 14 illustrates a seventh embodiment of the present invention, which is a variant to the FIG. 13 embodiment.

FIG. 14 shows a seventh embodiment of the present invention where it is seen that the means for introducing the fluid into the mixing vessel is now in the form of the same collapsible bag as that of FIG. 13, but now directly inserted into tubular agitator 6B once tightening rod 19 is removed, as is shown. Then, the U-shaped sleeve member 29 is removed from tube 26 so that fluid component A is drawn under vacuum down to the bottom of tubular agitator rod 6B, and mixed as previously described. An airtight adaptor means 42 is provided at the tube end so as to securely hold it within tube 26 during introduction of fluid A.

Figure 15:
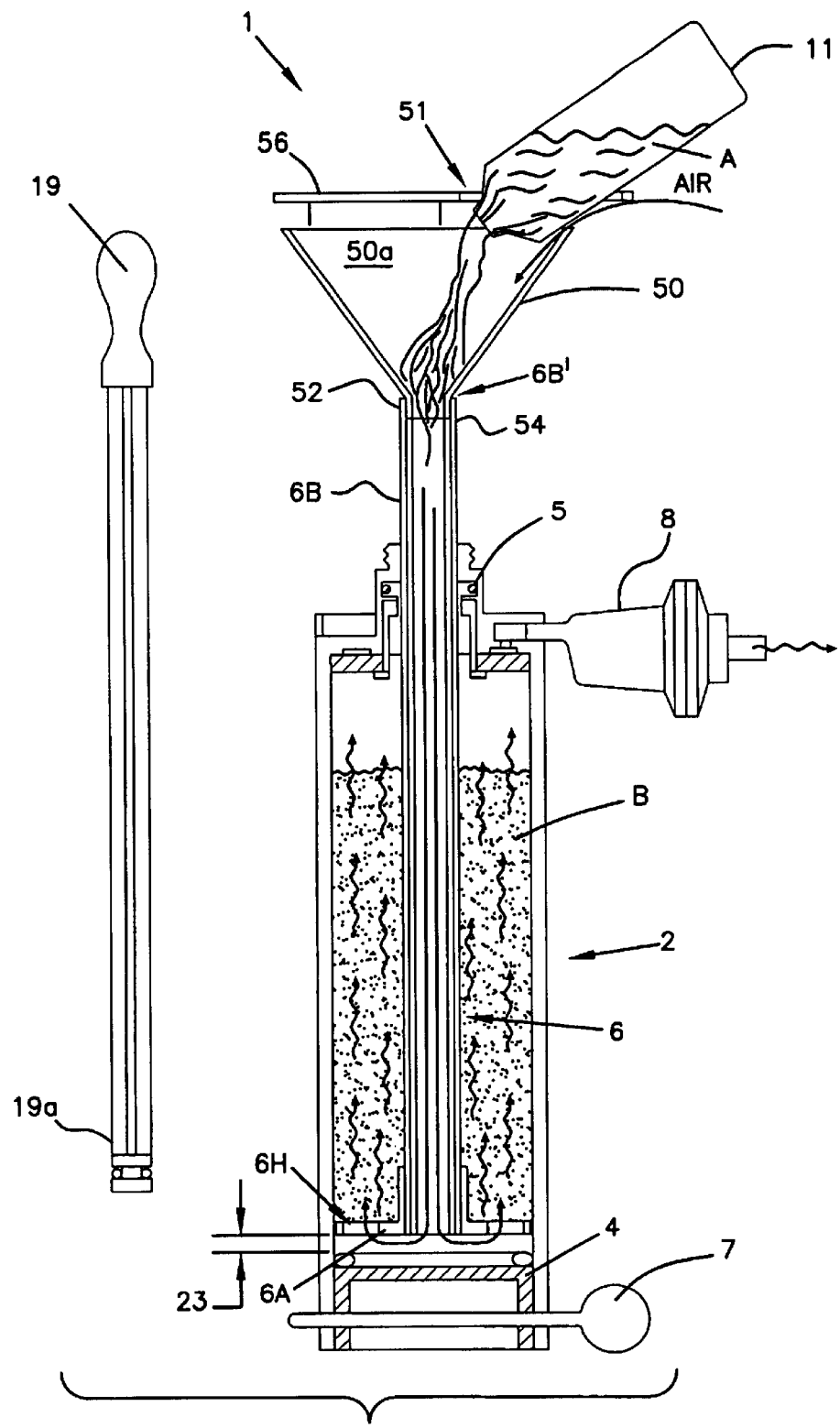
FIG. 15 illustrates the mixing vessel of an eighth embodiment of the present invention where the liquid form of the bone cement component is contained in a separate container and feed through a funnel to admix with the powder bone cement component.

FIG. 15 shows an eighth embodiment of the present invention where it is seen that the cylindrical containers 9 and 10 are eliminated so that once the glass ampoule 11 is broken, the liquid bone cement component A, is communicated into mixing vessel 2 via removable funnel member 50 and hollow agitator rod 6B. As seen, open funnel neck 52 is in frictional engagement with the open mouth 6B' of rod 6B when funnel 50 is inserted therein. The tip 11a of ampoule 11 is broken off and contents A are fed into funnel component receiving area 50a before descending down tube 6b. Again, this arrangement provides the liquid component at the container bottom so that both components can be pre-mixed together through percolation as previously explained. However, since there may be no longer an enclosure for sealing the ampoule once it is broken, in order to prevent atmospheric releases prior to mixing, the suction pressure on vacuum source 8 may be increased over that of the previous embodiments. High velocity ambient air entering the funnel will prevent fumes from escaping mixing vessel 2 into the surrounding environment. As a further means to prevent atmospheric escape, it is envisioned that funnel member 50 be provided with an O-ring or similar seal 54 about its open neck 52, and a cover 56 which contains an enlarged hole 51 for directing the liquid contents therethrough. In this way, the potential for fumes to escape between the rod 6B and funnel 50 are reduced by provision of cover 56, since they would be confined within the space between the cover and the funnel proper.

Figure 16:
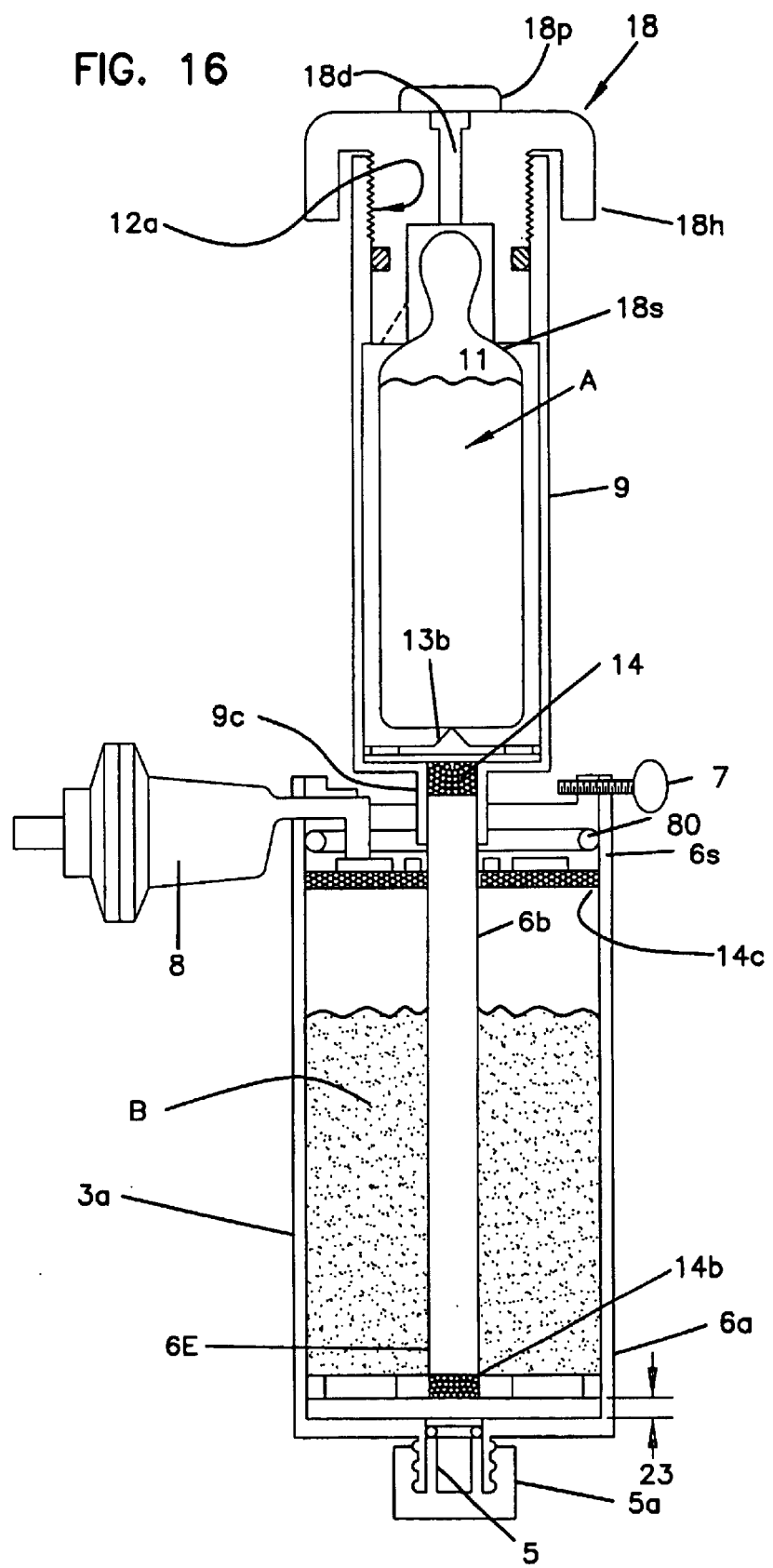
FIG. 16 illustrates the mixing vessel of a ninth embodiment of the present invention where the liquid cement container is inserted inside the tubular rod and joined thereto and the bone cement components are mixed by using the container as a handle for pulling and pushing the agitator inside the mixing chamber.
Figure 16A:
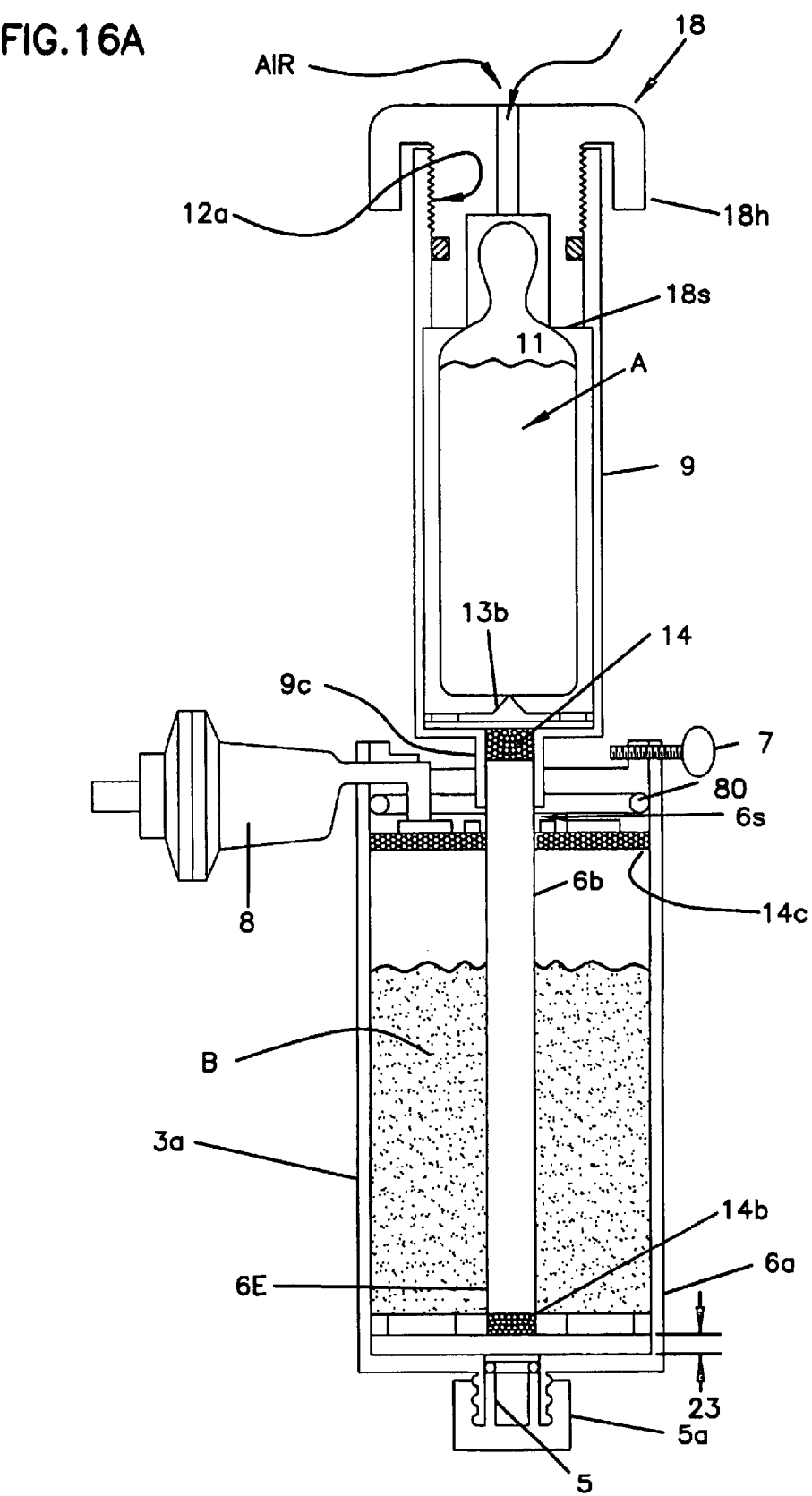
FIG. 16A illustrates the embodiment of FIG. 16 with a plug of the cap removed to allow air infiltration during mixing.
Figure 17:
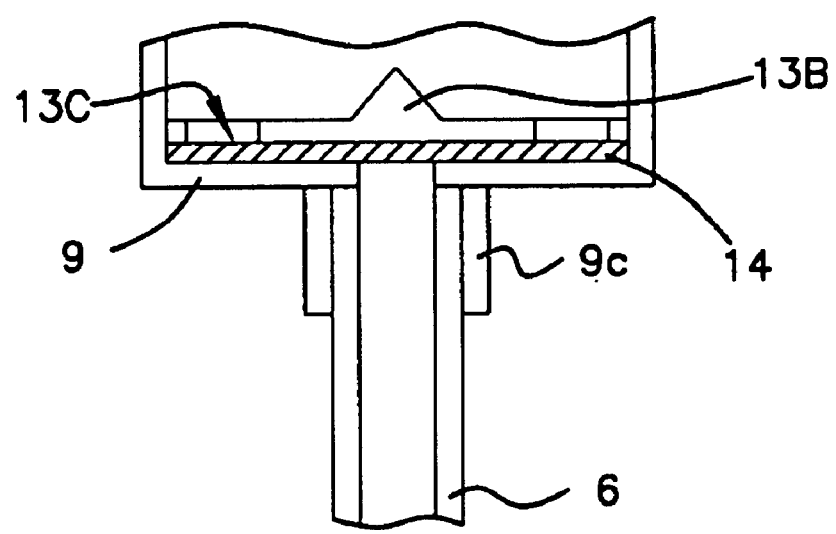
FIG. 17 illustrates a detailed view of the connecting area between the container and the tubular agitation rod.

FIGS. 16 and 16A show a final embodiment of the present invention, where it is seen that the container 9 and cap 18 as presented in FIGS. 9 and 10, is provided in FIG. 16 in a slightly modified fashion, where the glass ampoule 11 is now resting on breaking means 13 and that filter 14 is disposed below the breaking means. Furthermore, the container 9 is formed with a neck 9C that either inserts inside tubular rod 6b (similar to that of FIG. 4) or as shown here, is formed so that rod 6b inserts inside neck 9C. In either case, once the connection is made, the neck and the tube are joined together by known methods of friction spin-melting the like elastomeric components together, or they can be joined by conventional methods such as gluing, threading, or snap-fitting the pieces air-tight to each other. Once connected, the cap 18 gripping means 18h are operatively threaded downward along container threads 12a, until shoulders 18s cause the glass ampoule to be broken against pointed cone 13b of the breaking means. As FIG. 16A illustrates, once the ampoule 11 is broken, plug 18p is removed from cap 18 so that ambient air can be drawn into container 9 through action of suction device 8. Breaking of ampoule 11 will cause an air passage channel to form between shoulders 18s and ampoule, due to the ampoule slightly dropping after it is broken. Of course, part of the annular shoulders 18s could be provided with one of several relieved areas (dashed lines) to ensure that an air passage is provided. As explained earlier, the in-rush of ambient air will prevent fumes from escaping to the outside during the mixing process. The liquid component A passes from container 9, downwardly through filter 14, now located in neck 9c, then into hollow tubular member 6b, before passing through a second filter 14b at tube open end 6e. The liquid A then changes direction at the bottom of mixing vessel 2 due to the action of vacuum source 8 and turns upwardly to percolate into the powdered bone cement component B. Plug 18p is then re-inserted into opening 18d to seal container 9 from the atmosphere after contents A are emptied. The container 9 is then gripped as a handle and stroked up and down, thereby causing agitator disk 6a to mix the two bone cement components together, as previously explained with the other embodiments. As FIG. 16 shows, tubular element 6b is scored with an annular notch 6s, that allows the container-tubular rod to be separated from each other by snapping the container in a perpendicular direction to the rod, thereby breaking the rod at the notch. This step is performed after mixing is complete and after the tubular rod and agitator stick have been pulled back towards piston 80. Once the tubular element 6b is pulled back, mixing vessel 2 is turned upside down in order to facilitate removal of the mixed bone cement. A comparison of FIG. 16 to FIG. 9 makes this point more clear in that mixing vessel 2 in FIG. 16 is initially upside down such that spout 5 is sealed with a removable closure 5a and where the cylindrical container outer wall 3a also acts as the mixing vessel bottom, wherein the agitator 6 is inserted through the bottom of the container 3, rather than through the spout 5, as with the previous embodiments. With this arrangement, once the mixing is completed and the rod fractured at notch 6s, pin 7 is removed, as is vacuum source 8, so that piston 80 is advanced into contact with the bone cement mixture in the same manner as previously described with the other embodiments, and the mixture is pushed out of mixing vessel 2 through spout 5, of course once closure 5a is unthreaded and removed. A filter 14c rests against piston 80, thereby preventing cement from entering into the vacuum source and from escaping through the piston once it is advanced into contact with the cement. Spout 5 is used for attachment of various extrusion nozzles (not shown).

What is claimed is:

1. An apparatus for mixing batches of a liquid and a powder component for preparation of bone cement, comprising:

a mixing vessel pre-filled with the powder component of the bone cement, said vessel defined by an outer wall having a top end, a bottom end and an interior, said top end formed with a sealable spout, said bottom end formed with an axially displaceable bottom;

a vacuum source connected to the interior of said mixing vessel for maintaining the interior of said mixing vessel under vacuum;

an agitator at least partially disposed within said vessel interior, said agitator comprising a tubular rod which extends upwardly out of said interior through said spout, and an agitator disk attached to said tubular rod and disposed within the interior, a first end of said tubular rod being open and defining a mouth, and a second end of said tubular rod being open and encircled by said disk, and said tubular rod is axially displaceable within said vessel interior;

a generally cylindrical container having a top, a bottom, and an interior;

a glass ampoule having a sealed interior and a tip, said sealed interior containing the liquid bone cement component, said ampoule received within said interior of said container; and a cap secured to the top of said container, said cap having an opening therein whereby atmospheric air is communicated through said cap and into said interior of said container.

2. The apparatus according to claim 1, wherein said interior of said container including means for breaking said ampoule when said cap pushes on said ampoule, thereby allowing said container to feed said liquid component into said vessel.

3. A method for preparing bone cement by mixing batches of a liquid and a powder bone cement component, the method comprising the steps of:

providing a mixing vessel that is maintained under vacuum and that contains a pre-determined amount of the powder bone cement component, said vessel comprising a cylinder having an open interior with a spout at one end of said cylinder and having an axially displaceable bottom;

providing a mixing agitator within said vessel interior, said agitator comprised of a tubular rod having an agitator disk fixed on one end thereof, an opposite end of said tubular rod being open and defining a mouth, said mouth being located axially above said spout of said vessel, said agitator being axially displaceable within the vessel interior such that said agitator disk can mix the bone cement components together;

providing a tightening rod within said tubular rod so as to seal said vessel from atmosphere before said liquid component is introduced into said vessel;

removing said tightening rod and then introducing said liquid component into said interior of said vessel;

re-inserting said sealing rod within said tubular rod, thereby sealing said vessel from atmosphere; and axially displacing said agitator so as to mix said liquid and powder components under vacuum, without allowing harmful emissions to escape said mixing vessel.

4. The method of claim 3 further comprising providing a container that contains said liquid component, and placing said container in said mouth of said tubular rod.

5. An apparatus for preparing bone cement from liquid and powder bone cement components, comprising:

a mixing vessel pre-filled with the powder component of said bone cement, said vessel defined by an outer wall having a top end, a bottom end and an interior, said top end formed with a sealable spout, said bottom end formed with an axially displaceable bottom;

a vacuum source connected to the interior of said mixing vessel for maintaining the interior of said mixing vessel under vacuum;

means for introducing said liquid component into said interior of said mixing vessel through said sealable spout; and an agitator at least partially received within said vessel interior, said agitator comprised of a tubular rod which extends upwardly out of said interior through said spout and is in communication with the atmosphere and an agitator disk attached to said tubular rod, a first end of said tubular rod being open and defining a mouth and a second end of said tubular rod being open and encircled by said disk, said agitator disk is axially displaceable within said vessel interior for mixing said bone cement components.

6. The apparatus of claim 5 wherein said means for introducing said liquid component into said vessel is comprised of a container having an interior for containing said liquid component, a tip, and a tube connected to said tip, said tube connecting said container to said mixing vessel.

7. The apparatus of claim 6 wherein said tube is adapted to be inserted into said mouth of said tubular rod.

8. A method for introducing into a mixing vessel under partial vacuum a liquid component of bone cement to be mixed with a powder component of bone cement, the method comprising:
   providing a container which has an open interior, a threadable cap and means for breaking a glass ampoule;
   placing a glass ampoule containing said liquid component into said open interior;
   turning said cap for pushing downwards on said ampoule for breaking it against said means for breaking; and
   allowing said container to feed the liquid component through an opening in the container into said mixing vessel.

9. A method according to claim 8 further comprising connecting said container opening to the mixing vessel in an airtight manner, and allowing ambient air to enter into said open interior of the container through an opening in the cap of the container.

10. An apparatus for introducing into a mixing vessel under partial vacuum a liquid component of bone cement to be mixed with a powder component, wherein said apparatus comprises:
    a container which has an open interior for receiving at least one glass ampoule containing said liquid component and a threadable cap for pushing downwards on said ampoule, said interior including means for breaking said ampoule when said cap pushes on said ampoule.

11. An apparatus according to claim 10 wherein the container includes an opening that is adapted to be connected in an air tight manner to the mixing vessel, and wherein the cap has an opening for allowing ambient air to enter into said open interior of the container.

12. A method for feeding a liquid bone cement component into a mixing vessel maintained under vacuum for the preparation of bone cement wherein said mixing vessel is provided with a predetermined amount of a powder component of said cement, the method comprising the steps of:
    providing a mixing vessel defined by a cylindrical container having an open interior with a spout attached to one end of said container, and having an axially displaceable bottom;
    inserting a mixing agitator within said mixing vessel so as to communicate with said vessel interior, said agitator comprised of a tubular rod having an agitator disk fixed on one end thereof and having a second, open end defining a mouth, said mouth being located axially above said spoilt of said vessel, said agitator being axially displaceable such that said agitator disk can mix both of said bone cement components together;
    placing a container in said mouth of said tubular rod, said container having an interior space for receiving a glass ampoule and a threadable cap for pushing downwards on said ampoule, said interior space including a means for breaking said ampoule when said cap pushes on said ampoule thereby allowing said container to feed liquid into said vessel; and
    axially displacing said agitator so as to mix said liquid and powder components under vacuum, without allowing harmful emissions to escape said mixing vessel.

13. An apparatus for mixing a liquid and a powder component for the preparation of bone cement under vacuum in order to prevent harmful emissions from escaping once said liquid and powder components are mixed, comprising:
    a mixing vessel defined by an outer wall having a top end, a bottom end and an interior, said top end formed with a sealable spout, said bottom end formed with an axially displaceable bottom, said mixing vessel containing the powder bone cement component;
    means for introducing said liquid component into said interior of said mixing vessel through said sealable spout;
    an agitator at least partially received within said vessel interior, said agitator comprised of a tubular rod which extends upwardly out of said interior through said spout and is in communication with the atmosphere and an agitator disk with holes attached to said tubular rod, a first end of said tubular rod being open and defining a mouth and a second end of said tubular rod being open and encircled by said disk, said tubular rod being axially displaceable within said vessel interior for mixing said bone cement components;
    a removable tightening rod disposed within said tubular rod for sealing at least one open end thereof from communication with the atmosphere prior to and after said liquid component is introduced into said mixing vessel, said tightening rod being removed from said tubular rod immediately prior to introducing said liquid bone cement component into said mixing vessel and being reinserted therein after said liquid component is introduced within said mixing vessel; and
    wherein a gap is provided between the vessel bottom and the second end of said tubular rod for percolating an air/liquid mixture upwardly through the holes in the agitator disc to cause the liquid component to mix with the powder component.

14. The apparatus of claim 13, wherein said means for introducing said liquid component into said vessel comprises a container having an interior for containing said liquid component, an end of said container being insertable into said first end of said tubular rod.

15. A method for mixing a liquid and a powder bone cement component in a mixing vessel that is maintained under vacuum for the preparation of bone cement, the method comprising:
    providing a mixing vessel defined by a cylinder having an open interior with a spout attached to one end of said cylinder and having an axially displaceable bottom;
    providing a mixing agitator and inserting it within said spout so as to communicate with said vessel interior, said agitator comprised of a tubular rod having an apertured agitator disk fixed on one end thereof, an opposite end of said tubular rod being open and defining a mouth, said mouth being located axially above said spout of said vessel;
    providing a tightening means in said tubular rod so as to seal said vessel from said atmosphere;
    removing said tightening means and thereafter introducing said liquid component into said interior of said vessel;

re-inserting said sealing means within said tubular rod, thereby sealing said vessel from atmosphere;

axially displacing said agitator so as to mix said liquid and powder components under vacuum.

16. An apparatus for mixing liquid and powder bone components for preparation of bone cement, comprising:

a mixing vessel having an interior space defined by an outer wall having one end with a sealable opening, and an opposite end wit an axially displaceable wall;

a vacuum source connected to the interior space of said mixing vessel for maintaining the interior space under vacuum;

an agitator for mixing the liquid and powder bone cement components within the interior space of said mixing vessel, said agitator including an agitator disk disposed within the interior space and a tubular rod connected to said agitator disk and having an open end thereof extending through said sealable opening to the exterior of said mixing vessel, said agitator disk and said tubular rod are axially displaceable relative to said mixing vessel; and a feed arrangement for feeding the liquid or powder bone cement component into the interior space of said mixing vessel, said feed arrangement includes a container that contains the liquid or powder bone cement component within an interior thereof and said container includes an open end that is engageable with said open end of said tubular rod for feeding the liquid or powder bone cement component through the tubular rod into the interior space of said mixing vessel, and said container includes an aperture that places the interior of said container in communication with atmosphere.

17. The apparatus according to claim 16, wherein the interior of said container contains an ampoule holding the liquid bone cement component.

18. The apparatus according to clam 17, further comprising a cap secured to an end of said container opposite said open end thereof, said cap is engageable with said ampoule and is displaceable relative to said container for breaking said ampoule to release the liquid bone cement component.

19. The apparatus according to claim 18, wherein said aperture is provided in said cap.

* * * * *